(12) United States Patent
Meibaum et al.

(10) Patent No.: US 9,114,214 B2
(45) Date of Patent: Aug. 25, 2015

(54) EXTRACORPOREAL BLOOD TREATMENT APPARATUS

(75) Inventors: Joern Meibaum, Lohfelden (DE); Gerhard Bock, Friedewald (DE)

(73) Assignee: B. BRAUN AVITUM AG, Melsungen (DE)

( * ) Notice: Subject to any disclaimer, the term of this patent is extended or adjusted under 35 U.S.C. 154(b) by 309 days.

(21) Appl. No.: 13/994,379

(22) PCT Filed: Dec. 14, 2011

(86) PCT No.: PCT/EP2011/006312
§ 371 (c)(1),
(2), (4) Date: Aug. 22, 2013

(87) PCT Pub. No.: WO2012/079755
PCT Pub. Date: Jun. 21, 2012

(65) Prior Publication Data
US 2013/0331758 A1    Dec. 12, 2013

(30) Foreign Application Priority Data

Dec. 14, 2010 (EP) ..................................... 10015621

(51) Int. Cl.
*A61M 37/00* (2006.01)
*A61M 1/30* (2006.01)

(52) U.S. Cl.
CPC .................. *A61M 1/30* (2013.01); *A61M 1/302* (2014.02); *A61M 1/303* (2014.02); *A61M 1/306* (2014.02)

(58) Field of Classification Search
CPC ....... A61M 1/30; A61M 1/302; A61M 1/303; A61M 1/306; A61M 1/14; A61M 1/16; A61M 1/3627; A61M 1/3643
USPC ................................................. 604/4.1–6.16
See application file for complete search history.

(56) References Cited

U.S. PATENT DOCUMENTS 4,596,550 A    6/1986    Troutner
4,643,714 A *    2/1987    Brose ........................... 604/6.05

(Continued)

FOREIGN PATENT DOCUMENTS

CN    1436087    8/2003

(Continued)

OTHER PUBLICATIONS

Decision on Grant for RU 2013129870/14(044403) with translation dated Dec. 5, 2014.

(Continued)

*Primary Examiner* — Philip R Wiest
(74) *Attorney, Agent, or Firm* — RatnerPrestia (57) ABSTRACT

The invention relates to an extracorporeal blood treatment apparatus with
a control device (50) for controlling the opening and closing of an arterial line (2) with simultaneous closing and opening of a venous line (3) in a single-lumen-arrangement (10), with which untreated blood is removed through the single-lumen-arrangement (10) and the arterial line (2), led through a blood treatment device (5) and treated blood is fed back through the venous line (3) and the single-lumen-arrangement (10),
an arterial line container (20) which is arranged in the arterial line (2) in front of the blood treatment device (5),
a venous line container (30) which is arranged in the venous line (3) following the blood treatment device (5),
a sensor device (31) for detecting an amount of treated blood being above a limit value in the venous line container (30),
a sensor device (21) for detecting an amount of untreated blood being below a limit value in the arterial line container (20),
an arterial line closure device (22) for closing the arterial line (2) with simultaneous opening of the venous line (3) in response to a signal A which is transmitted by the sensor device (31) to the arterial line closure device (22),
a venous line closure device (32) for closing the venous line (3) with simultaneous opening of the arterial line (2) in response to a signal B which is transmitted by the sensor device (21) to a venous line closure device (32) and
at least one pump (40) and is characterized in that a control device (50) is provided, with which a phase volume $V_{act}$ is adjustable automatically in dependence on the current pumping rate $Q_{BP}$ of the at least one pump (40) during a phase to a predefined value $V_{nom}$ (FIG. 1).

10 Claims, 4 Drawing Sheets

(56) References Cited

U.S. PATENT DOCUMENTS 5,318,511 A 6/1994 Riquier et al.
7,981,280 B2 * 7/2011 Carr et al. .................... 210/134

FOREIGN PATENT DOCUMENTS

| | | |
|---|---|---|
| CN | 1678360 | 10/2005 |
| CN | 101466419 | 6/2009 |
| DE | 34 22 375 | 1/1985 |
| GB | 2 141 936 | 1/1985 |
| JP | 2000-299 | 7/2001 |
| RU | 2258452 | 3/2005 |

OTHER PUBLICATIONS

Translation of Chinese Examination Report for CN 201180060059.4 dated Dec. 3, 2014.

International Search Report for PCT/EP2011/006312 dated Mar. 6, 2012.

* cited by examiner

EXTRACORPOREAL BLOOD TREATMENT APPARATUS

CROSS REFERENCE TO RELATED APPLICATIONS

This application is the U.S. national phase application of PCT International Application No. PCT/EP2011/006312 filed Dec. 14, 2011, which claims priority to European Application No. 10 015 621.5 filed Dec. 14, 2010, the contents of each application being incorporated by reference herein.

FIELD OF THE INVENTION

The invention relates to an extracorporeal blood treatment apparatus.

DESCRIPTION OF THE RELATED ART

Such an apparatus is known, for example from DE 34 22 375 A1. The apparatus described therein has a single lumen catheter, by which the extracorporeal blood treatment apparatus is connectable to the blood circulation of a patient to be treated. Due to the single lumen connector of the patient to the apparatus it is necessary that the blood sampling and the reinfusion of the blood are performed through this single-lumen connector.

In DE 3422375 A1 several possibilities of extracorporeal arrangement of tubes, pressure sensors, clamps and pumps are shown. Critical for all these arrangements is that they have on the one hand an arterial line container after an arterial tube clamp and on the other hand a venous line container in front of a venous tube clamp. Both containers form a blood reservoir so that even with closure of one of both tube clamps blood can be continuously passed through the dialyzer. The control between arterial phase, in which the blood is taken from the patient and supplied to the blood treatment apparatus, and venous phase, in which the taken blood is reinfused into the patient, is performed depending on an arterial and a venous pressure sensor which are attached to the arterial line container and venous line container, respectively.

Thereby, during the arterial phase the arterial tube clamp is open and the venous is closed. A blood pump conveys thereby the blood to be purified through the tube system into the dialyzer and further into the venous line container towards the closed venous tube clamp. Once in the venous line container the pressure has reached a predetermined upper limit, the arterial phase is terminated, and the venous phase is started by opening the venous tube clamp and closing the arterial. By the blood pump blood is now passed from the arterial line container into the dialyzer and further into the venous line container while purified blood from the venous line container is reinfused into the patient. This is performed until the negative pressure constituting in the arterial line container has reached a lower limit. Now in turn the arterial tube clamp is opened and the venous one is closed, so that from now on the venous phase is terminated and a new phase consisting of a fresh arterial and a fresh venous phase begins.

Another apparatus is described in the US patent U.S. Pat. No. 4,643,714. This is in principle identical in its construction with the apparatus described already in DE 3422375 A1. So also here an extracorporeal arrangement of tubes, pressure sensors, clamps, and a pump is disclosed, in which analogous an arterial line container is arranged after an arterial tube clamp and on the other hand a venous line container in front of a venous tube clamp. Both containers also form a blood reservoir.

The control between arterial phase, in which the blood taken from the patent and passed into the blood treatment apparatus, and venous phase, in which the taken blood is reinfused into the patient, is performed here depending on an arterial pressure sensors at the arterial line container in order to switch from the arterial phase to the venous phase, and other than in DE 3422375 A1 depending on the measured displaced volume in order to switch from the arterial phase to the venous phase. Furthermore, this apparatus comprises a protective mechanism in which the pump is turned off in the arterial phase if reaching a determined over-pressure in the venous line container in order to avoid damage to the dialyzer.

US patent U.S. Pat. No. 5,318,511 describes, however, a system of an extracorporeal arrangement of tubes, pressure sensors, blood reservoir container and pumps, in which the control between arterial phase and venous phase is regulated by a pressure measurement at the venous line container (transition from venous to arterial phase) and a predefined pump rotation speed (transition from venous to arterial phase) However, the method described therein is significantly more complex and up to four pumps are needed, wherein two pumps are assigned respectively for the arterial or venous phase. A regulation or control for automatic flow regulation in case of occurring disturbances is, however, not disclosed in this US patent.

Basically, the apparatuses described in the documents DE 3422375 A1, U.S. Pat. Nos. 4,643,714 and 5,318,511 or the methods described therein work satisfactory, as long as no disturbances occur in the extracorporeal circulation, especially in the tube system. A disturbance in the system and an automatic recovery under the maintenance of a continuous blood treatment is not mentioned in regard to the above-described apparatuses and this is also not considered further. Just U.S. Pat. No. 4,643714 discloses an automatic stop of the pump in case of total failure of the system in order to protect the dialyzer.

The apparatuses described in the state of the art are however, not capable to adjust automatically the phase volume by the pumping rate of the pump in case of disturbances in order to maintain the operation of the apparatus. Such a disturbance can be represented on the one hand for example, by a kink in the arterial or venous tube line. On the other hand, such a disturbance can also have its reason in a wrong setting of the blood pump speed by the operator, wherein also the start of therapy should be considered as such a disturbance. In the extreme case such disturbances can result in that no effective blood flow-out of the patient body and back into, takes place or takes no longer place. In the following such a disturbance is described shortly exemplary based on a kink in the venous tube line:

By a kink in the venous tube line during the venous phase the flow resistance increases there, by which the outflow of the purified blood into the patient decreases and the venous line container is emptied correspondingly slower. As a result, the arterial phase volume is reduced over several phases, because with the same blood flow through the dialyzer until reaching the low pressure limit in the arterial line container the venous line container is not appropriately emptied. Consequently, the upper pressure limit in the venous line container is reached increasingly earlier during the following phases. The entire system therefore begins to oscillate between arterial and venous phase without an effective blood flow through the extracorporeal blood purification machine occurring. Therefore in such situations, especially taking into account the dead volume as described below, effectively no reinfusion of already purified blood into the patient is carried out. Thus, no more therapy takes place in these situations with the extracorporeal blood purification machine described in DE 3422375 A. This can only be prevented if the operator intervenes regulating.

The consequences of a kink in the venous tube line will be also described in the following referring to the apparatus of U.S. Pat. No. 4,643,714. By the obstruction of the blood flow in the venous tube line during the venous phase, the venous line container can be emptied only insufficiently and with running pump and constant blood feeding from the dialyzer, the pressure in the venous line container increases rapidly. However, this is not considered for a change to the arterial phase and the change is performed only upon a certain negative pressure in the arterial line container. The venous line is subsequently closed and the arterial line is open. Since the accumulated liquid volume in the venous line container could not flow out during the venous phase, the predetermined limit for the pressure of the venous line container is achieved immediately with the running pump. In achieving the limit, the pump is turned off and the arterial line container is filled without pump performance due to the negative pressure existing there. If a defined amount of blood is flowed into the arterial line container and if this amount corresponds to a predefined limit for the displaced volume, so the pump is activated automatically and a change in the venous phase starts by closure of the arterial line and opening of the venous line. It has thus been set a critical state in which the venous line container and the arterial line container are completely filled, and additionally an obstruction of the venous line exists. A regulation of the pump performance in the venous phase does not exist, and with the running pump and increasing pressure in the venous line container, the system is finally escalated because a new change to the arterial phase is associated only with a certain negative pressure in the arterial line container. This can only be prevented if the operator intervenes regulating.

Also the apparatus described in U.S. Pat. No. 4,596,550 could not automatically counteract a disturbance, e.g. a kink in the venous line. By the obstruction of the blood flow in the venous tube line it would immediately result in an escalation of the system, since between the venous line container and the patient access an additional pump is interposed, which is responsible for the pumping process of the dialyzed blood from the venous line container into the patient. Because there is no sensor system for the flow resistance behind this pump, the pump performance cannot be adjusted to the given conditions. An escalation of the system can also here only be prevented, when the operator intervenes regulating.

In the last two examples it is thus to be emphasized that there is a lack of a control system within the apparatuses that compensates a disturbance especially during a venous phase.

SUMMARY OF THE INVENTION

Thus, an extracorporeal blood treatment apparatus is provided, which despite occurring disturbances in the blood flow system, the therapy can be continued and also in case of elimination or removal of the disturbance the apparatus can automatically pass to a more effective performance.

DETAILED DESCRIPTION OF THE INVENTION

This problem is solved by an apparatus with the features described herein. Advantageous embodiments of the invention are claimed and set forth in the examples and the figures.

In contrast to the above cited prior art, the present invention is characterized by an automated control system, in which depending on the currently delivered blood volume of a phase (arterial or venous) and its deviation from a defined nominal value ($V_{nom}$), a disturbance is automatically detected and by continuous adjustment of the pump performance (up-and down-regulation), the operation of the apparatus for extracorporeal blood treatment can be maintained, as the nominal value of the phase volume ($V_{nom}$) is adapted to the actual value of the phase volume ($V_{act}$) by adjusting the pumping rate $Q_{BP}$ of at least one pump (40) by means of a control device (50).

As used herein, following terms have the following meanings:

$t_{Phase}$: Is the period of a phase from the opening of the arterial line closure device 22 to the next opening of the arterial line closure device 22.

$t_{Art\_Phase}$: Is the period of the arterial phase from the opening of the arterial line closure device 22 to the closing of the arterial line closure device 22.

$t_{Ven\_Phase}$: Is the period of the venous phase from the opening of the venous line closure device 32 to the closing of the venous line closure device 32.

$V_{Phase}$: Phase volume: Is the volume conveyed by the pump during the period of a phase.

$V_{act}$: Actual value of the phase volume: The actual value of the phase volume is the phase volume conveyed actually during a phase, which corresponds in a faultless dialysis process to the nominal value of the phase volume and deviates with occurring disturbances from the nominal value.

$V_{nom}$: Nominal value of the phase volume: The nominal value of the phase volume is predetermined for the first phase at the beginning of the dialysis, e.g. by the operator or automatically determined based on reference values of previous dialysis sessions and can definitely also vary. For each other phase, the nominal value of the phase volume corresponds to the actual value of the phase volume of the previous phase.

$\Delta V$: Difference between the actual value of the phase volume and the nominal value of the phase volume. If $\Delta V>0$, in the current phase a larger phase volume than in the previous phase was conveyed. If $\Delta V<0$, in the current phase a smaller phase volume than in the previous phase was delivered.

$Q_{BP}$: Is the pumping rate of the pump (40), indicated in mL/s.

Thus the present invention refers to an extracorporeal blood treatment apparatus with a control device (50) for controlling the opening and closing of an arterial line (2) with simultaneous or substantially simultaneous closing and opening of a venous line (3) in a single-lumen-arrangement (10), with which untreated blood is taken through the single-lumen-arrangement (10) and the arterial line (2), passed through a blood treatment device (5) and treated blood is fed back through the venous line (3) and the single-lumen-arrangement (10), an arterial line container (20) which is arranged in the arterial line (2) in front of the blood treatment device (5), a venous line container (30) which is arranged in the venous line (3) following the blood treatment device (5), a sensor device (31) for detecting an amount of treated blood being above a limit value in the venous line container (30), a sensor device (21) for detecting an amount of untreated blood being below a limit value in the arterial line container (20), an arterial line closure device (22) for closing the arterial line (2) with simultaneous or substantially simultaneous opening of the venous line (3) in response to a signal A which is transmitted by the sensor device (31) to the arterial line closure device (22), a venous line closure device (32) for closing the venous line (3) with simultaneous or substantially simultaneous opening of the arterial line (2) in response to a signal B which is transmitted by the sensor device (21) to a venous line closure device (32) and at least one pump (40) for conveying a phase volume $V_{Phase}$ with a pumping rate $Q_{BP}$, wherein if the actually conveyed phase volume $V_{act}$ deviates from the phase volume $V_{nom}$, the control device (50) regulates then the pumping rate $Q_{BP}$ of the at least one pump (40) so that this deviation $\Delta V$ tends to be nil.

That the arterial line container (20) is arranged in the arterial line (2) in front of the blood treatment device (5) means that the arterial line container (20) is in blood flow direction forwards the blood treatment device (5) and thus is arranged between arterial line closure device (22) and blood treatment device (5).

In all embodiments of the herein disclosed extracorporeal blood treatment apparatus, the feature an arterial line container (20), which is arranged in the arterial line (2) in front of the blood treatment device (5), can be replaced as follows by:

an arterial line container (20), which is arranged in the arterial line (2) in blood flow direction towards the blood treatment device (5), or by an arterial line container (20), which is arranged in the arterial line (2) between arterial line closure device (22) and blood treatment device (5).

Preferably, the arterial line container (20) is arranged between arterial line closure device (22) and pump (40).

That the venous line container (30) is arranged in the venous line (3) following the blood treatment device (5) means that the venous line container (30) is in blood flow direction behind the blood treatment device (5) and thus is arranged between venous line closure device (32) and blood treatment device (5).

In all embodiments of the herein disclosed extracorporeal blood treatment apparatus, the feature a venous line container (30), which is arranged in the venous line (3) following the blood treatment device (5), can be replaced as follows by:

a venous line container (30), which is arranged in the venous line (3) in blood flow direction behind the blood treatment device (5), or by a venous line container (30), which is arranged in the venous line (3) between venous line closure device (32) and blood treatment device (5).

The term "simultaneous" or "substantially simultaneous" means that the closing of the arterial line closure device (22) is performed at the same time as the opening of the venous line closure device (32) and correspondingly the closing of the venous line closure device (32) takes place at the same time as the opening of the arterial line closure device (22). Thus, a continuous blood flow is maintained. Preferably, the term "at the same time" describes that both processes, i.e. closing of 32 and opening of 22 as well as closing of 22 and opening of 32 take place within a second.

The feature a sensor device (31) for detecting an amount of treated blood being above a limit value in the venous line container (30), means that a upper limit for contained treated blood, or a filling level, or a maximum pressure correlating with the filling level should be detected, whereby it is indicated that the venous line container (30) contains a predetermined maximum amount of liquid and thus is full and now the emptying should be initiated. Thus, the above-mentioned feature may be replaced in all herein described embodiments by:

a sensor device (31) for detecting the filling level in the venous line container (30), or a sensor device (31) for detecting a maximum filling level in the venous line container (30), or a sensor device (31) for detecting if a predetermined filling level in the venous line container (30) has been reached, or a sensor device (31) for detecting a maximum pressure in the venous line container (30), or a sensor device (31) for detecting if a predetermined pressure in the venous line container (30) has been reached.

The feature a sensor device (21) for detecting an amount of untreated blood being below a limit value in the arterial line container (20), means that a lower limit for untreated blood contained, or a filling level, or a minimum pressure correlating with the filling level or negative pressure should be detected, whereby it is indicated that the arterial line container (20) contains a predetermined minimum amount of liquid and thus is empty and now the filling should be initiated.

Thus, the above-mentioned feature may be replaced in all herein described embodiments by:

a sensor device (21) for detecting the filling level in the arterial line container (20), or a sensor device (21) for detecting a minimum filling level in the arterial line container (20), or a sensor device (21) for detecting if a predetermined filling level in the arterial line container (20) has been reached, or a sensor device (21) for detecting a minimum pressure or a negative pressure in the arterial line container (20), or a sensor device (21) for detecting if a predetermined pressure or negative pressure in the arterial line container (20) has been reached, The feature of an arterial line closure device (22) for closing the arterial line (2) with simultaneous or substantially simultaneous opening of the venous line (3) in response to a signal A which is transmitted by the sensor device (31) to the arterial line closure device (22), means that the sensor device (31), as above-described, measures a filling level or maximum filling level or a predetermined pressure or a predetermined over-pressure or verifies the achievement of such a predetermined limit values and after reaching the predetermined filling level or pressure transmits a signal to the control device (50) which then regulates the closing of the arterial line closure device (22) and simultaneous opening of the venous line closure device (32). Above feature can therefore be replaced by one of the following formulations:

an arterial line closure device (22) for closing the arterial line (2) with simultaneous opening of the venous line (3)

in response to a signal A which is transmitted by the sensor device (31) via the control device (50) to the arterial line closure device (22), or an arterial line closure device (22) for closing the arterial line (2) with simultaneous opening of the venous line (3) in response to a signal A which is transmitted by the control device (50) to the arterial line closure device (22).

The feature of a venous line closure device (32) for closing the venous line (3) with simultaneous or substantially simultaneous opening of the arterial line (2) in response to a signal B which is transmitted by the sensor device (21) to a venous line closure device (32), means that the sensor device (21), as above-described, measures a filling level or minimum filling level or a predetermined pressure or a predetermined negative pressure or verifies achievement of such a predetermined limit value and after achieving the predetermined filling level or pressure transmits a signal to the control device (50) which then regulates the closing of the venous line closure device (32) and the simultaneous opening of the arterial line closure device (22).

Above feature can therefore be replaced by one of the following formulations:

a venous line closure device (32) for closing the venous line (3) with simultaneous opening of the arterial line (2) in response to a signal B which is transmitted by the sensor device (21) via the control device (50) to a venous line closure device (32), or a venous line closure device (32) for closing the venous line (3) with simultaneous opening of the arterial line (2) in response to a signal B which is transmitted by the control device (50) to a venous line closure device (32).

The present invention refers, thus, to an extracorporeal blood treatment apparatus with a control device (50) for controlling the opening and closing of an arterial line (2) with simultaneous closing and opening of a venous line (3), with which untreated blood can be taken through the arterial line (2), can pass through a blood treatment device (5) and can be fed back as treated blood through the venous line (3), an arterial line container (20) which is arranged in the arterial line (2) in front of the blood treatment device (5), a venous line container (30) which is arranged in the venous line (3) behind the blood treatment device (5), a sensor device (31) for detecting the filling level of treated blood in the venous line container (30), a sensor device (21) for detecting the filling level of untreated blood in the arterial line container (20), an arterial line closure device (22) for closing the arterial line (2) with simultaneous opening of the venous line (3) in response to a signal A which is transmitted by the sensor device (31) via the control device (50) to the arterial line closure device (22), a venous line closure device (32) for closing the venous line (3) with simultaneous opening of the arterial line (2) in response to a signal B which is transmitted by the sensor device (21) via the control device (50) to a venous line closure device (32) and at least one pump (40) for conveying a phase volume $V_{Phase}$ with a pumping rate $Q_{BP}$, wherein if the actually conveyed phase volume $V_{act}$ deviates from the phase volume $V_{nom}$, the control device (50) regulates then the pumping rate $Q_{BP}$ of the at least one pump (40), so that this deviation $\Delta V$ tends to be nil.

In other words, the present invention refers to an extracorporeal blood treatment apparatus with a control device (50) for controlling the opening and closing of an arterial line (2) with simultaneous closing and opening of a venous line (3), with which untreated blood can be taken through the arterial line (2), can pass through a blood treatment device (5) and can be led back as treated blood through the venous line (3), an arterial line container (20) which is arranged in the arterial line (2) in front of the blood treatment device (5), a venous line container (30) which is arranged in the venous line (3) behind the blood treatment device (5), a sensor device (31) for detecting the filling level of treated blood in the venous line container (30), a sensor device (21) for detecting the filling level of untreated blood in the arterial line container (20), an arterial line closure device (22) for closing the arterial line (2) with simultaneous opening of the venous line (3) in response to a signal A which is transmitted by the sensor device (31) via the control device (50) to the arterial line closure device (22), a venous line closure device (32) for closing the venous line (3) with simultaneous opening of the arterial line (2) in response to a signal B which is transmitted by the sensor device (21) via the control device (50) to a venous line closure device (32) and at least one pump (40) for conveying a predefined phase volume $V_{nom}$ with a pumping rate $Q_{BP}$ during a phase with a phase period $t_{Phase}$, wherein if the actually delivered phase volume $V_{act}$ deviates from the phase volume $V_{nom}$ within a phase, the control device (50) regulates then the pumping rate $Q_{BP}$ of the at least one pump (40) during the subsequent phase, so that this deviation /W tends to be nil.

The above-mentioned characterized part can also be alternatively formulated as follows:

wherein the control device (50) regulates the pumping rate $Q_{BP}$ of the at least one pump (40) during the subsequent phase, if the actually delivered phase volume $V_{act}$ deviates from the phase volume $V_{nom}$ within a phase, so that $V_{act}$ is adjusted to $V_{nom}$, or wherein the control device (50) regulates, if the actually delivered phase volume $V_{act}$ deviates from the phase volume $V_{nom}$ within a phase, the pumping rate $Q_{BP}$ of the at least one pump (40), so that $V_{act}$ is adjusted to $V_{nom}$.

or wherein the control device (50) is designed to set a phase volume depending on the current pumping rate $Q_{BP}$ of the at least one pump (40) during a phase, automatically to a predefined $V_{nom}$, wherein the same control device (50) is designed as a control circuit with which the phase volume is controllable to a definable nominal value $V_{nom}$, wherein the deviation $\Delta V$ of an actual value $V_{act}$ of the phase volume from its nominal value $V_{nom}$ is used for regulation, and wherein the regulation with a change of the performance of the pump (40) includes an automatic adjustment of the actual value $V_{act}$ of the phase volume to its nominal value $V_{nom}$ and the associated change of the time period of a phase $t_{Phase}$, wherein said regulation can be performed in the venous phase as well as in the arterial phase.

The nominal value of the phase volume $V_{nom}$ of the current phase is the actual value of the phase volume $V_{act}$ of the previous phase. If the blood flows unhindered and there is no constriction in the arterial line (2) and/or the venous line (3), the nominal value of the phase volume $V_{nom}$ corresponds to the actual value of the phase volume $V_{act}$ and $\Delta V$ is nil or taking into account a certain tolerance range is approximately nil.

If, however, a constriction occurs during a phase in the area of the arterial line (2) in the section between patient and the arterial line container (20) and/or in the area of the venous line (3) in the section between venous line container (30) and patient, then, the phase volume $V_{act}$ actually conveyed in the phase, where the constriction has occurred, is smaller than in the previous phase, i.e., $V_{nom}$ is larger than $V_{act}$ and thus $\Delta V = V_{act} - V_{nom} < 0$.

Thus, during the previous phase a larger phase volume was conveyed than in the current phase and the phase volume $V_{act}$ actually conveyed during the current phase is in regard to the following phase the nominal value of the phase volume $V_{nom}$. In order that in the following phase, the actual value of the phase volume $V_{act}$ achieves the nominal value of phase volume $V_{nom}$, the pumping rate of the pump (40) is reduced in a way that in the subsequent phase, the volume $\Delta V$ is conveyed less. If in the following phase, the actual value of the phase value $V_{act}$ achieves the nominal volume of the phase volume $V_{nom}$, this means that no further constriction has occurred, but the existing constriction has not been expanded or has not expanded itself. However, if the constriction advances or another constriction appears, so the actual value of the phase volume $V_{act}$ in the following phase is also smaller than the nominal value of the phase volume $V_{nom}$ and $\Delta V$ is again below zero.

The inventive apparatus in the herein described embodiments can thus, independently and automatically regulate the blood flow in case of constrictions in the area of the lines between venous line container (30), patient and arterial line container (20) in order to maintain the process of the dialysis and without interrupting the dialysis session or require the intervention of nursing staff by warning. The requirement for this automatic control of the pumping rate of the pump (40) is that the constriction in the arterial line (2) between patient and arterial line container (20) is not so strong that the blood flows more slowly in the arterial line container (20) as the pump (40) removes it again from the arterial line container (20). This would be such a strong disturbance, that a warning would be issued and the dialysis would have to be interrupted. Preferably, the pump (40) is then automatically switched off. The same applies if the constriction in the venous line (3) between venous line container (30) and patient would be so strong that the blood flows more slowly from the venous line container (30) as the pump (40) supplies blood into the venous line container (30). This is also a continuing fault condition which results in the output of a warning and shut down of the pump (40).

If the apparatus, according to aspects of the invention, comprises more than one pump (40), so the additional pump (40) or the further pumps (40) is located between the dialyzer (5) and the venous line container (30) or between the arterial line container (20) and the dialyzer (5). All pumps (40) run then preferably at the same pumping rate $Q_{BP}$ and are regulated simultaneously by the control device (50).

If an existing constriction is now expanded again, for example, by the nursing staff or even by itself by movement of the patient, this causes that during the current phase, a larger phase volume is transported than in the previous phase. Thus, at the end of the current phase, the nominal value of the phase volume $V_{nom}$ is less than the actual volume of the phase volume $V_{act}$ and thus $\Delta V > 0$. This results automatically in increasing the pumping rate $Q_{BP}$ by the volume $\Delta V$ during the following phase, in order that the nominal value of the phase volume $V_{nom}$ corresponds again in the following phase with the actual value of the phase volume $V_{act}$ in the following phase.

According to aspects of the invention, therefore, is that with slower outflow of the blood from the venous line container (30) the pumping rate of the pump (40) can be reduced automatically and that in case of a re-improved outflow of the blood from the venous line container (30), the pumping rate of the pump (40) can be automatically increased again, without the need of operator intervention to the control or readjustment thereof. The same applies also for a disturbed inflow of the blood in the arterial line container (20).

Another alternative formulation of the invention reads as follows, wherein the invention refers to an extracorporeal blood treatment apparatus with a control device (50) for controlling opening and closing of an arterial line (2) with simultaneous closing and opening of a venous line (3) in a single-lumen-arrangement (10), with which untreated blood can be taken through the arterial line (2), can be passed through a blood treatment device (5) and treated blood can fed back through the venous line (3), an arterial line container (20) which is located in the arterial line (2) between the arterial line closure device (22) and the blood treatment device (5), a venous line container (30) which is located in the venous line (3) between the blood treatment device (5) and the venous line closure device (32), a sensor device (31) for detecting the filling level in the venous line container (30) and a signal transduction to the control device (50), a sensor device (21) for detecting the filling level in the arterial line container (20) and a signal transduction to the control device (50), an arterial line closure device (22) for closing the arterial line (2) with simultaneous opening of the venous line (3) in response to a signal A which is transmitted by the control device (50) to the arterial line closure device (22), if the filling level of the venous line container (30) has achieved a defined threshold value, a venous line closure device (32) for closing the venous line (3) with simultaneous opening of the arterial line (2) in response to a signal B which is transmitted by the control device (50) to a venous line closure device (32), if the filling level of the arterial line container (20) has achieved a defined threshold value, and at least one pump (40) for conveying a predefined phase volume $V_{Phase}$ with a pumping rate $Q_{BP}$, wherein the control device (50) regulates the pumping rate $Q_{BP}$ of the at least one pump (40), if the actually conveyed phase volume $V_{act}$ deviates from the phase volume $V_{nom}$ with a deviation $\Delta V$, in a way that this deviation $\Delta V$ tends to be nil.

According to aspects of the invention, the pumping rate $Q_{BP}$ of the pump (40) or the pumps (40) is not changed during a current phase, but respectively at the beginning of a subsequent phase, as long as in the previous phase a $\Delta V$ results being unequal to zero or greater than a predefined tolerance interval of, for example 1 mL. Thus, in case of a $\Delta V < 0$, the pumping rate of the pump (40) or the pumps (40) is reduced at the beginning of the subsequent phase by the volume ΔV, i.e., if it is assumed that the phase duration of the subsequent phase corresponds to the phase duration of the current phase, the pumping rate of the pump (40) or the pumps (40) is reduced at the beginning of the subsequent phase, so that during the phase duration of the subsequent period in total the volume ΔV is conveyed less.

Figure 1:
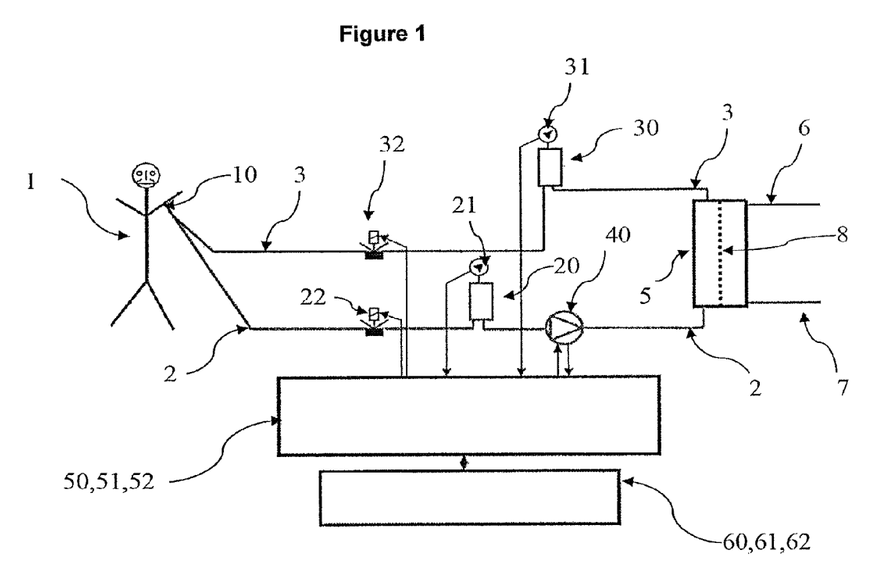
FIG. 1: a schematic representation of an embodiment of an inventive device with a patient already connected
Figure 2:
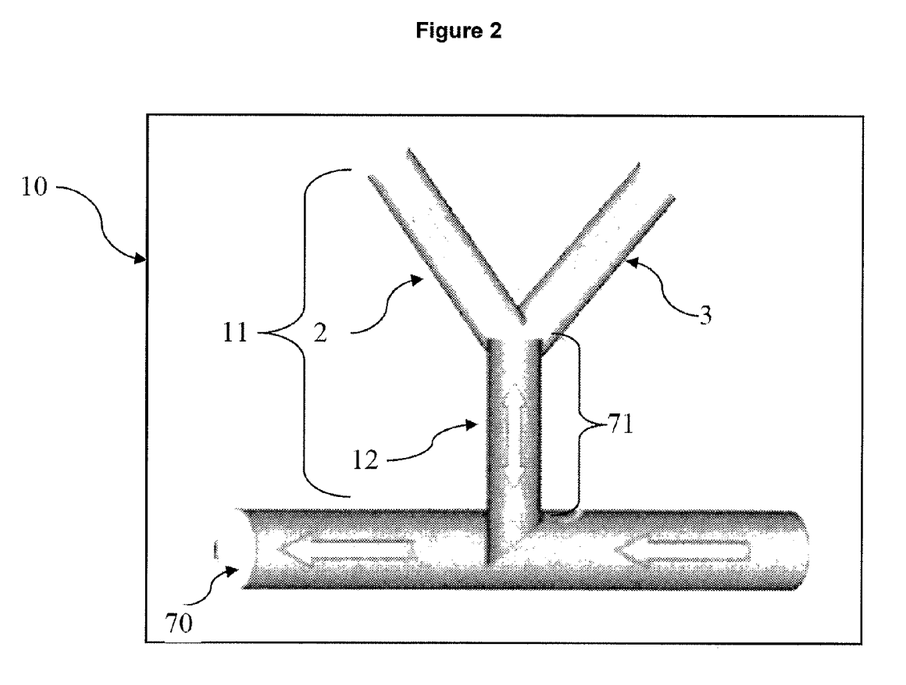
FIG. 2: a schematic representation of an embodiment of a single-lumen-arrangement 10 connected to the vascular system of a patient.

According to aspects of the invention, the single-lumen-arrangement (10) is defined in this document, as particularly obvious from FIG. 1, as an arrangement of a patient access (12) at the vascular system (70) of the patient (s. FIG. 2), with a Y-piece (11) (s. FIG. 2), as well as the arterial line (2) connected thereto and the venous line (3), wherein the arterial line (2) directs through the arterial line container (20) and the pump (40) to the blood treatment device (5), and the venous line (3) directs from the blood treatment device (5) through the venous line container (30) via the Y-piece (11) to the patient. Thereby the single-lumen-arrangement (10) can realize the access to the patient for example, by means of a needle or a flexible indwelling cannula.

A phase refers to the time period which is between opening of the arterial line closure device (22) until the next opening of the arterial line closure device (22), and is defined as sum of the arterial phase and the venous phase. Thereby, the arterial phase describes the time period between opening of the arterial line closure device (22) and closing of the arterial line closure device (22), and the venous phase describes the time period between opening of the venous line closure device (32) and closing of the venous line closure device (32).

The apparatus is wherein the control device (50) is designed as control circuit with which the automatic adjustment of the actual value $V_{act}$ of the phase volume to its nominal value $V_{nom}$ and the associated change of the time period of a phase t -phase can be performed in the venous phase as well as in the arterial phase.

In addition, it is wherein the controller of the control circuit is designed as P-controller, I-controller, D-controller, PI-controller, PD-controller, PID-controller, two-point controller, three-point controller, multi-point controller or fuzzy-controller.

The nominal value $V_{nom}$ of the phase volume is thereby at least 5 times, preferably at least 10 times larger as a dead volume $V_{dead}$ (71) of the single-lumen-arrangement (10).

The control device (50) is designed in such a manner that it delays the regulation of the phase volume directly after detection of a deviation $\Delta V \neq 0$ of the actual value $V_{act}$ of the phase volume from its nominal value $V_{nom}$ by a predetermined dead time $T_{dead}$, wherein the predetermined dead time $T_{dead}$ is lasting thereby at least two phases, preferably at least four phases and maximum 10 phases.

The at least one pump (40) is located between the arterial line container (20) and the venous line container (30). The sensor devices (21, 31) are designed preferably as pressure sensors and the over-pressure measured by the sensor device (31) in the venous line container (30) triggers closing of the arterial line closure device (22) and opening of the venous line closure device (32) and the negative pressure measured by the sensor device (21) in the arterial line container (20) triggers closing of the venous line closure device (32) and opening of the arterial line closure device (22).

For the determination of the actual value $V_{act}$ of the phase volume, thereby the pumping rate $Q_{BP}$ of the pump (40) as well as the time period of a phase $t_{Phase}$ is used, wherein the time period of a phase $t_{Phase}$ is defined as sum of the time period $t_{Ven\_Phase}$ which lasts between the signal A and the signal B, which are transmitted by the control device (50) to the arterial line closure device (22) and the venous line closure device (32), and the time period $t_{Art\_}$Phaser which lasts between the signal B and the signal A which are transmitted by the control device (50) to the arterial line closure device (22) and the venous line closure device (32).

The same definition as it is described in the beginning for DE 3422375 A1 forms the basis for used terms of the arterial and venous phase wherein instead of arterial and venous tube clamps herein it is based more generally on arterial line and venous line closure devices.

For the effective operation of blood treatment apparatuses it is important that the treated, accumulated blood volume is as large as possible. The special feature of the one lumen or single lumen operation reduces a volume which is defined by the single-lumen connector of the blood treatment apparatus to the vascular system of the patient and will be referred to as dead volume, the treated volume of blood. Since the already purified blood in the single lumen patient access, i.e., the dead volume is fed back into the extracorporeal dialyzer again during the arterial phase, the effectiveness of the treatment decreases. The blood contained in this dead volume $V_{dead}$ is called recirculation volume because during each arterial phase, a certain amount of blood due to the existing clearance volume in the extracorporeal circuit is not reinfused into the patient's body. This dead volume is caused by the single lumen patient access, to which Y-piece connects for merging the arterial and venous tube system. Basically, the higher the recirculation, the lower is the clearance performance. A recirculation proportion less than 10% of the phase volume is deemed to be a normal range. Another factor within the single needle/single lumen operation is the phase volume $V_{Phase}$ The phase volume $V_{Phase}$ results from the blood volume in the arterial phase $V_{Art\_Phase}$, which is taken from the patient or the blood volume in the venous phase $V_{Ven\_Phase}$ that is returned to the patient. The blood volume of the arterial and venous phase differs by the liquid volume that is removed from the blood in the dialyzer by ultrafiltration.

The effective blood volume $V_{eff}$ newly fed to the dialyzer from the patient's body during a phase is therefore, calculated as:

$$V_{eff} = V_{Art\_Phase} - V_{dead}.$$

The determination of the phase volume $V_{Phase}$ is performed by multiplication of the pumping rate $Qg_p$ of the blood pump and the time period $t_{Phase}$ t of a phase as:

$$V_{Phase} = Q_{BP} * t_{Phase}$$

wherein the time period $t_{Phase}$ of a phase results from the addition of the time period of the arterial phase $t_{Art\_Phase}$ and the time period of the venous phase $t_{Ven-Phase}$ as:

$$t_{Phase} = t_{Art\_Phase} + t_{Ven\_Phase}.$$

From the pumping rate $Q_{BP}$ of the blood pump, the arterial flow $Q_{Art\_Blood}$ as well as the venous flow $Q_{Ven\_Blood}$ are to be distinguished, which cooperate also with the phase volume according to following equations. It is:

$$V_{Phase} = V_{Art\_Phase} + V_{Ven\_Phase}, \text{ wherein with}$$

$$V_{Art\_Phase} = Q_{Art\_Blood} * t_{Art\_Phase} \text{ and}$$

$$V_{Ven\_Phase} = Q_{Ven\_Blood} * t_{Ven\_Phase}$$

for $V_{Phase}$ following relation applies:

$$V_{Phase} = Q_{BP} * (t_{Art\_Phase} + t_{Ven\_Phase})$$

The accumulated blood volume which is taken from the patient during the therapy and reinfused again, results as:

$$V_{Therapy} = Q_{Art\_Blood} * t_{Art\_Phase} * t_{Therapy} / (t_{Art\_Phase} + t_{Ven\_Phase})$$

wherein the total dead volume $V_{dead\text{-}total}$ add up over the total therapy as:

$$V_{dead\text{-}total} = V_{dead} * t_{Therapy} / (t_{Art\_Phase} + t_{Ven\_Phase}).$$

For the effectively treated blood amount in the single needle/single lumen operation it has therefore become apparent being advantageous, according to aspects of the invention, to define the phase volume on the basis of the used vascular access and adapt the blood flow continuously to a predefined or predetermined value. It is thus ensured that for a predetermined vascular access, the optimum blood flow is achieved, in which the recirculation proportion is, for example, less than 10%. Thus, this invention improves the quality of the therapy and contributes to the maximum amount of treated blood. This is realized in that within the device according to aspects of the invention a control device is provided, with which a phase volume is adaptable automatically to a predefined or predetermined value $V_{nom}$ depending on the current pumping rate $Q_{BP}$ of the at least one blood pump during a phase.

Therefore, the blood volume $V_{act}$ conveyed during a phase is determined and compared with the predefined or predetermined value $V_{nom}$. If no difference between $V_{act}$ and $V_{nom}$ can be determined, the therapy continues as in the phase for which $V_{act}$ was last determined. If, however, a difference $\Delta V = V_{nom} - V_{act} \neq 0$ is determined, then by the control device of the inventive apparatus it is initiated that the pumping rate of the blood pump is changed correspondingly, so that in the subsequent phase the phase volume is affected in the direction of predefined or predetermined value $V_{nom}$.

Thereby it should be considered that the arterial line closure device as well as the venous line closure device are still opened or closed when reaching the threshold values detected by the sensor devices associated to the arterial or venous line containers. If, however, the blood volume $V_{act}$ conveyed during a phase is below the nominal value $V_{nom}$, contrary to the increase to be expected a decrease of the pumping rate of the pump is carried out. The reason is that the failure to reach the nominal value $V_{nom}$ is not caused by a flow rate of the pump being too low, but thereby that the predetermined limit has been reached in the arterial or venous line container too early and therefore the arterial or venous phase ends, although the blood volume $V_{nom}$ to be conveyed has not been reached during this phase. Therefore, according to aspects of the invention the phase volume is adjusted by the control device in dependence on the actual pumping rate $Q_{BP}$ of at least one pump to a predefined value $V_{nom}$, that by a reduction of the pumping rate $Q_{BP}$ the time period is increased, in which the predetermined threshold value will be achieved in the arterial or venous line container. In this increased period of the arterial or venous phase, the system has now more time to reach the corresponding, predefined value $V_{nom}$ for the phase volume. If in the subsequent phases, the phase volume is still below this predefined value $V_{nom}$ the pumping rate of the pump is reduced again accordingly. In order to achieve a correspondingly uniform treatment, it is of course also possible to increase the pumping rate $Q_{BP}$, of the least one pump if the blood volume $V_{act}$ conveyed during a phase is above the nominal value $V_{nom}$.

Besides the influencing variables mentioned already at the beginnings such as disturbances in the tube system and in the pumping rate of the pump, a viscosity change of the blood also affects the phase volume. Also, such disturbances are to be handled in a simple manner with the device according to aspects of the invention as adjusting the phase volume using the device according the invention at the beginning of blood treatment in a patient.

In practice, it has been proven to design the control device as control circuit in which the phase volume is automatically controllable to a nominal value, wherein the deviation $\Delta V$ of an actual value $V_{act}$ of the phase volume from its nominal value $V_{nom}$ is used for regulation. Advantageously, the controller of the control circuit is designed as a P-controller, I-controller, D-controller, PI-controller, PD-controller, PID-controller, two-point controller, three-point controller, multi-point controller or fuzzy-controller. Due to the large selection of these various controller types, it is possible in a simple manner to adjust the regulation also very fine so that even a smallest $\Delta V$ values results in an intervention of the control and thus the phase volume can be kept approximately constant during the entire therapy, whereby an optimal treatment is guaranteed. The individual mathematical formulations of the various controllers have been omitted here, since the embodiment of a respective controller and the constant factors to be used therewith can vary depending on the used device according to aspects of the invention and their determination is at the discretion of the person skilled in the art.

Furthermore it is advantageous to keep the nominal value $V_{nom}$ of the phase volume at least five times, preferably at least ten times as large as the dead volume of the single-lumen-assignment 10. This ensures that the largest possible effective blood volume is purified during the entire therapy.

In another embodiment of the invention, it has been proven as reasonable to carry out the regulation of the phase volume time-shifted. For this purpose the control device is designed such that it delays the regulation to the phase volume directly after detection of a deviation $\Delta V \neq 0$ of the actual value $V_{act}$ of the phase volume from its nominal value $V_{nom}$ by a predetermined dead time $T_{dead}$. By this measure it is avoided that the regulation responds unnecessarily, if the deviation $\Delta V \neq 0$ is within a tolerance range. This maybe caused, for example, by systemic influences, such as by using a roller pump not constantly conveying due to its construction, or by short-term disturbances such as a short-term kink in the arterial and/or venous line. The dead time $T_{dead}$ should therefore not be determined absolutely, but should be defined according to a certain number of predetermined phase, consisting as previously described respectively of an arterial and a venous phase.

In practice, it has therefore been proven as advantageous to define this dead time at least as two such phases, preferably as four such phases and maximum as ten such phases.

To minimize the equipment requirements, it is advantageous to use only one pump which has to be located between the arterial line container and the venous line container. Thereby a defined blood conveyance is guaranteed in both the arterial and the venous phase with only one pump in the system, which is very economical not only in terms of production and acquisition cost, but also in terms of maintenance work.

In a particular embodiment of the invention, it has been proven as advantageous that the sensor devices allocated to the arterial line and the venous line containers are designed as pressure sensors. Thus, in a simple manner by negative or over-pressure in the arterial line or venous line container their filling level can be determined and by means of the control device or the pumping rate of the pump and the time passed between opening and closing or respectively the blood conveyed during this time period the actual value $V_{act}$ for the phase volume can be determined.

Further objects, advantages, features and applications of the present invention result from the following description of embodiments with reference to the drawings. Thereby all described and/or illustrated features establish for themselves, or in any meaningful combination the subject-matter of the present invention, regardless of their summarization in the claims and their dependencies.

DETAILED DESCRIPTION OF THE PREFERRED EMBODIMENTS

In FIG. 1 an embodiment of an extracorporeal blood treatment apparatus according to aspects of the invention is represented schematically. In this representation, a patent 1 to be treated is connected by a single-lumen-arrangement 10 to the apparatus. The single-lumen-arrangement 10, as in particular seen in FIGS. 1 and 2, includes the arrangement of a patient access 12 at the blood vascular system 70 of the patient, with a Y-piece 11, as well as the arterial line 2 and the venous line 3 connected to it, wherein the arterial line 2 goes through the arterial line container 20 and the pump 40 towards the blood treatment device 5, and the venous line 3 goes through the venous line container 30 to the blood treatment device 5. Thereby the single-lumen-arrangement 10 can realize the access to the patient, for example, by means of a needle or a flexible indwelling cannula.

During the therapy, blood is taken from the vascular system 70 of the patient 1 by means of the patient access 12 of the single-lumen-arrangement 10. From the patient access 12 the blood to be purified enters, as shown in FIG. 1, through the arterial line 2 into an arterial line container 20, wherein it passes an arterial line closure device 22 located in the arterial line 2. From the arterial line container 20 the blood is now conveyed further along the arterial line 2 extending up to a blood treatment device 5. In this embodiment the conveyance of blood from the arterial line container 20 is performed by means of a pump 40 which can be designed, for example, as roller pump. In the blood treatment device 5 the actual purification of the blood takes place, as through diffusion and/or convection toxic substances and/or fluid is eliminated from the blood. The purification of the blood is performed herein by a semi-permeable membrane 8 arranged in the blood treatment device 5. The blood to be purified flows in this embodiment in counter flow through the semipermeable membrane to a dialysate fed by a dialysate inlet 6 of the blood treatment device 5. By a dialysate outlet 7 located at the blood treatment device 5 the spent dialysate enriched with the toxins eliminated from the blood to be purified, is fed back to a collection device not shown. The purified blood is removed from the blood treatment device 5 by means of an arranged venous line 3 and conveyed into a venous line container 30. From there the purified blood is fed through a continuation of the venous line 3, wherein it passes a venous line closure device 32 located in the venous line 3, again to the single-lumen-arrangement 10. Here, the purified blood is reinfused now through the patient access 12 of Y-piece 11 almost completely back into the vascular system 70 of the patient 1 to be treated.

In a extracorporeal blood treatment apparatus with a single-lumen-arrangement 10 as access to the vascular system 70 of the patient 1, however, it is not possible, due to this particular configuration, to take simultaneously blood to be purified from the patient 1 as well as to reinfuse the purified blood into the patient 1. Therefore, extracorporeal blood treatment apparatuses with single-lumen-arrangement 10 are equipped, as described in this embodiment, with special control and sensor elements which enable at times alternately to take blood to be purified from the patient 1 and to reinfuse purified blood. To this control and sensor elements, besides the already mentioned arterial line and venous line closure devices 22, 32 and the pump 40, belong sensor devices 21, 31 associated to the arterial line container 20 or the venous line container 30, by which a statement of the filling level in each container 20, 30 can be obtained. Further even a control device 50, a monitoring device 51, a reservoir device 52, a display device 60, an input device 61, as well as a communication device 62 belong to them.

The communication direction of this respective control and sensor elements is shown in FIG. 1 by arrow. Thus, the group consisting of control device 50, monitoring device 51 and reservoir device 52 receives data from the sensor elements 31 and 21. Based on this data, the elements of this group and particularly the control device 50 can transmit instructions to the closure device 22 and 32 as well as the pump 40 to change their current operating state. Furthermore, the control device 50, the monitoring device 51 and the reservoir device 52 can exchange bidirectionally data and information with the display device 60, the input device 61 as well as the communication device 62.

Hereinafter, the operation mode of the embodiment according to FIG. 1 is described, wherein it is not refer to the beginning of the therapy, but to the operation mode during an already running therapy. Beginning with an arterial phase, the situation in the normal operation without disturbance is represented as follows:

During the arterial phase, the arterial line closure device 22 is opened, so that blood taken from patient 1 by means of the single-lumen-arrangement 10 can flow through the arterial line 2 into the arterial line container 20. At the beginning of an arterial phase, there is a negative pressure in the arterial line container 20 which makes sure that the blood is sucked in from the patient and the arterial line container 20 is filled up to a certain filling level, where a pressure equalization between the negative pressure in the arterial line container 20 and the blood pressure of the patient has been occurred. From this time point the arterial line container 20 does not filled anymore and blood is replenished to the extend it is conveyed by the pump 40 from the arterial line container 20. Simultaneously, the pump 40 conveys the blood existing in the arterial line container 20 further through the continuation of the arterial line 2 into the blood treatment device 5 designed as dialyzer, where substances are removed from the blood toxic by means of diffusion and/or convection as well as the weight of the patient is reduced by the fluid removed by means of ultrafiltration. From there, the now already treated blood passes through the venous line 3 into the venous line container 30. Since in the arterial phase, the venous line closure device 32 is closed, the blood being in the venous line container 30 cannot flow off and be reinfused through the single-lumen-arrangement in the vascular system 70 of the patient 1. Due to the closed venous line closure device 32, the venous line container 30 is filled with already treated blood, until a certain upper filling level defined by a threshold value is achieved in the venous line container 30. This threshold value is determined in the present embodiment according to FIG. 1 by the sensor device 31 designed as pressure sensor based on a predefined over-pressure inside the venous line container 30. If this over-pressure value is transmitted by the pressure sensor 32 to the control device 50, this causes simultaneously (signal A) closing of the arterial line 2 by the arterial line closure device 22 and opening of the venous line 3 by the venous line closure device 32.

Thus, the arterial phase is at an end and the venous phase begins, in which already treated blood is reinfused into the patient 1. This occurs at the beginning of each venous phase by the over-pressure developed in the venous container 30 until a time point, where a pressure balance between the blood pressure of the patient and the over-pressure in the venous line container 30 has achieved. From this time point on the venous line container 30 is emptied only to the extend the pump 40 pumps new, purified blood into the venous line container 30. In the venous phase, the venous line 3 is not closed anymore by the venous line closure device 32 so that the already treated blood being in the venous blood container 30 is reinfused into the vascular system 70 of the patient. The venous line container 30 empties thus, due to the over-pressure present in the venous line container 30 and the continuous conveyance of the blood by the pump 40 into the venous line container 30. Under normal conditions (no disturbance in the venous line), the outflow from the venous line container 30 is larger than the inflow into the venous line container 30. By conveyance of the pump 40, not only the venous line container 30 is continuously supplied with blood, but also the arterial line container 20 is emptied. This continues until a certain lower filling level defined by a threshold value is reached in the arterial line container 20. This threshold value is detected in the present embodiment according to FIG. 1 by the sensor device 21 designed as pressure sensor based on a predefined negative pressure inside the arterial line container 20.

If this negative pressure value is transmitted by the pressure sensor 21 to the control device 50, this causes simultaneously (signal B) closing of the venous line 3 by the venous line closure device 32 and opening of the arterial line by the arterial line closure device 22.

Thus, the venous phase is now also at the end and during this phase consisting of arterial and venous phase the pump 40 has conveyed the phase volume $V_{act}=V_{nom}$ substantially within certain tolerance limits. This operation mode described so far represents the desired operation mode without disturbance. At the beginning of the next phase consisting of arterial and venous phase, in the patient access 12 of the Y-piece 11 (figure. 2) of the single-lumen-arrangement 10 is already treated blood, which is then fed in the arterial phase back into the purification circuit in the extracorporeal blood purification device, without previously being reinfused to the patient 1 again. Thus, the volume of patient access 12 is also called dead volume 71, since in an extracorporeal blood purification apparatus with a single-lumen-arrangement 4, it is inevitable that the blood existing at the end of the venous phase in this dead volume 71, without previously being reinfused into the vascular system 70 of the patient 1, is again subject to a purification circuit.

It is therefore of particular interest to keep the ratio of phase volume $V_{act}$ to the dead volume (71) $V_{dead}$ as large as possible or as close as possible to the value $V_{nom}/V_{dead}$ Therefore, it is desirable that in case of occurring disturbances, particularly in the tube system of the extracorporeal blood purification apparatus, the apparatus as soon as possible performs automatically appropriate actions. Hereinafter the automatic regulation of this embodiment will be described with reference to a disturbance in the tube system of extracorporeal blood purification apparatus based on a kink in the venous line 3 between the Y-piece 11 and the venous line container 30 beginning in the venous phase.

By the kink at this position in the venous line 3, there increases the flow resistance for the blood that is emptied from the venous line container 30 and thus flows during the venous phase slower than without kink. The outflow from the venous line container 30 is in case of a disturbance which the system can automatically react to, slower than without the disturbance but still faster than the inflow determined by the pump. Thus, the ratio of outflow and inflow from the venous line container 30 shifts in favor of the inflow, whereby the fluid volume in the venous line container 30 is not decreased but increased At the same time, the arterial line container 20 is emptied further with the closed arterial line closure device 22 by the continued delivery of the pump 40 until the predefined threshold value for the negative pressure is reached in the arterial line container 20. Now, by the control device 50 the arterial line closure device 22 is opened and the venous line closure device 32 is closed so that the venous phase is terminated and the arterial phase begins. Thereby that during the venous phase due to the kink a slower emptying of the venous line container 30 has occurred than in the undisturbed system, the filling level is there at the beginning of the arterial phase in comparison to the undisturbed extracorporeal circuit higher so that with unchanged pumping rate of the pump 40, the predefined limit value for the over-pressure in the venous line container 30 is reached more quickly. This means that the arterial phase volume is low in comparison to the undisturbed system because the control device 50 ends the arterial phase if the sensor device 31 detects the predefined threshold value for the over-pressure in the venous line container 30 and forwards it to the control device 50. In the subsequent venous phase, this scenario is repeated in case of continued disturbance. Because the emptying of the venous line container 30 is still slowed down, the filling level in the venous line container 30 is at the end of this venous phase even higher than in the previous phase, so that in the now following arterial phase even less blood would be conveyed by the pump 40 into the venous line container 30. Without an intervention of the regulation according to aspects of the invention, the system would now escalate and, in extreme case, both in the venous line container 30 and in the arterial line container 20 the predefined threshold values would be reached immediately after switching by the control device 50 from the arterial to the venous phase, or vice versa, and no more phase volume would be conveyed. In order to counteract this by using the control, monitoring and reservoir devices 50, 51 and 52, the deviation ΔV of the actual value $V_{act}$ of the phase volume conveyed by the pump 40 during one phase of arterial and venous phase from the nominal value $V_{nom}$ stored in the reservoir device 52 is determined. In this case, the deviation ΔV is positive and if it is outside of a predefined tolerance range, the control circuit then intervenes into the system and causes the control device 50 to reduce the pumping rate of the pump 40 by a certain amount. By the now lower pumping rate of the pump 40, less blood volume is conveyed into the venous line container 30 during a venous phase, so that—if necessary after several cycles or phases consisting of arterial and venous phase only—the blood volume defined by emptying of the venous line container 30 during a venous phase is larger than the blood volume conveyed in this venous phase by the pump 40 into the venous line container 30. By this measure, the absolute times for the venous and arterial phase increase, so that although the pumping rate of the pump 40 is reduced, the blood volume conveyed by the pump 40 in a phase consisting of arterial and venous phase and thus the phase volume $V_{act}$ is increased. If the phase volume $V_{act}$ is again within the tolerance range of $V_{nom}$, the controller no longer affects. The phase volume $V_{act}$ was thus configured automatically by the control circuit without the intervention of the user in the tolerance range of the nominal value $V_{nom}$.

If the disturbance—present kink in the venous line 2—is removed, then the control circuit intervenes again. The now lower flow resistance would result in an increase of the phase volume so that the control device 50 by the control circuit would increase the pumping rate of the pump 40, until the phase volume $V_{act}$ is again in the tolerance range of the nominal value $V_{nom}$.

Thus, it is possible to maintain the therapy with the apparatus according to aspects of the invention, as long as in the extracorporeal blood circuit a circulation still takes place and the disturbance blocks the tube system not completely.

Figure 3:
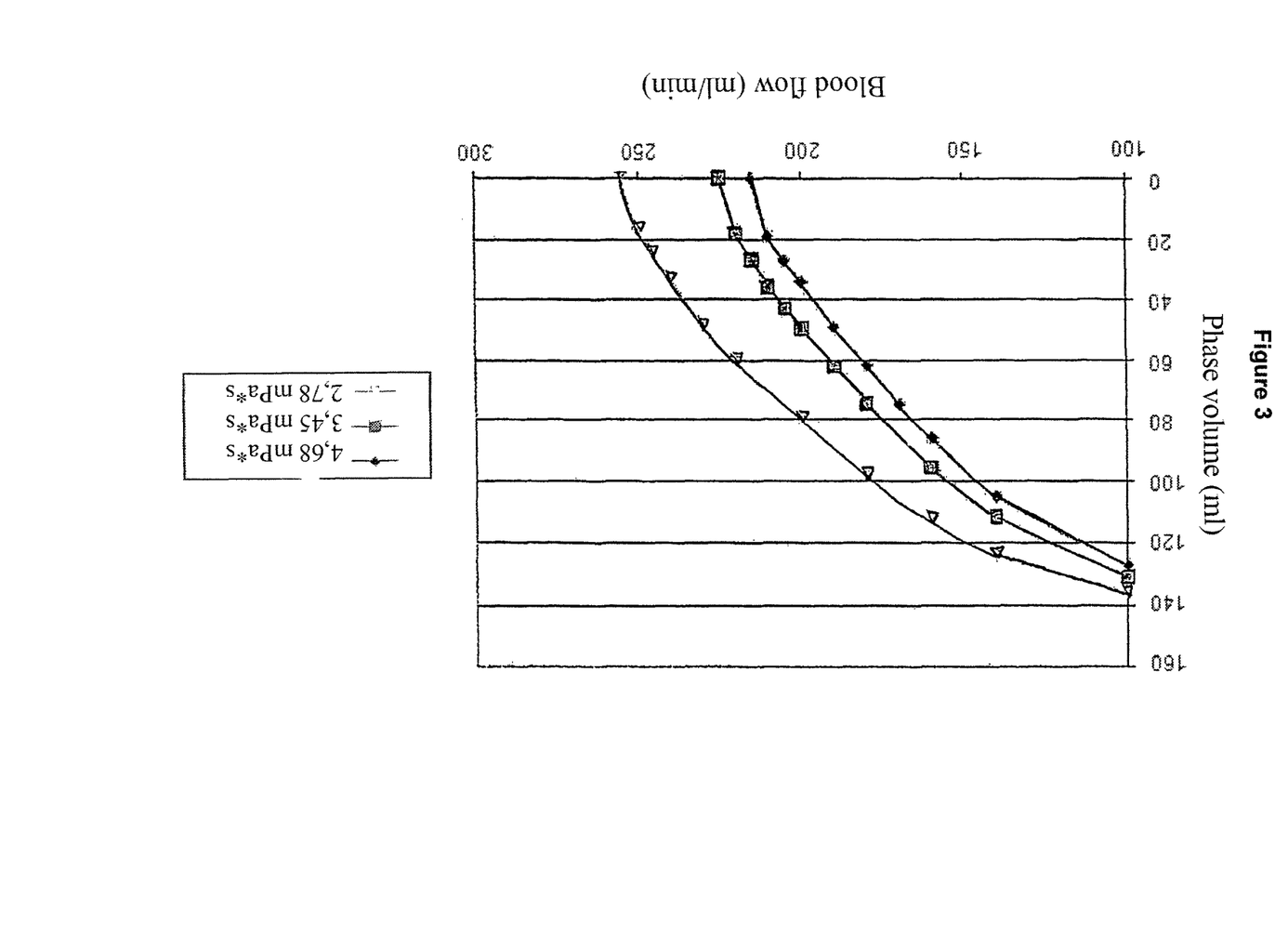
FIG. 3: representation of the dependence of the phase volume on the pumping volume of the blood pump for various blood viscosities.

A change in the viscosity of the blood of the patient 1 during a therapy can also be considered as a disturbance in the broader sense. As shown in FIG. 3, namely the phase volume relates to the blood flow differently for various viscosities. Viscosity changes during a therapy occur naturally also by the unavoidable fluid loss of the patient 1. Such viscosity changes cause a change of the flow resistance in the tube system of the apparatus, too, which are considered as disturbance, since thereby the amount of the ratio of $V_{act}/V_{dead}$ is reduced and thus the effectiveness of the treatment is deteriorated. Also, such a disturbance occurring by viscosity change of the blood during the therapy of the patient 1 can be affected correspondingly by the control circuit, so that the optimum effectiveness of the therapy is achieved.

Figure 4:
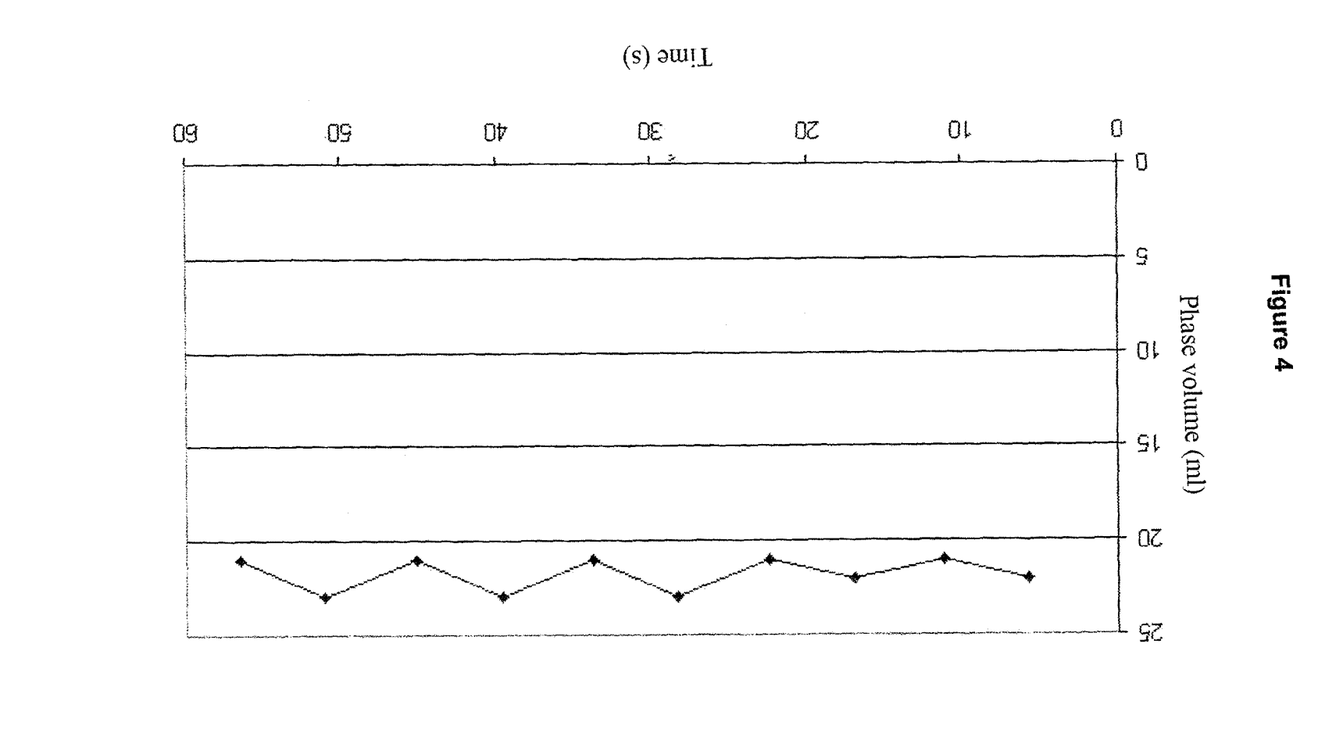
FIG. 4: Example of a signal fluctuation of the phase volume in dependence on the time when using a roller pump.

In FIG. 4 is shown exemplarily, the behavior of the phase volume $V_{act}$ in the undisturbed state over time using a roller pump 40 being common in the field of the extracorporeal blood treatment. The fluctuations of the phase volume $V_{act}$ shown there, which are caused by the construction and the physical conditions of a roller pump 40, are the reason why it is not regulated to an exact nominal value $V_{nom}$, but to a tolerance range or tunnel around such a nominal value. The background for this purpose is that by the using a roller pump deviations of the phase volume $V_{act}$ are unavoidable. Such deviations should not already cause that the phase volume $V_{act}$ is regulated to the nominal value $V_{nom}$. Only when the actual value of the phase volume $V_{act}$ leaves the predetermined tolerance range or tunnel, the control circuit should intervene in order to ensure the best possible effectiveness of therapy with the best possible efficiency.

The invention claimed is:

1. Extracorporeal blood treatment apparatus with:
   a control device for controlling opening and closing of an arterial line with simultaneous closing and opening of a venous line in a single-lumen-arrangement, with which untreated blood is taken through the single-lumen-arrangement and the arterial line, passed through a blood treatment device and treated blood is fed back through the venous line and the single-lumen-arrangement;
   an arterial line container which is arranged in the arterial line in front of the blood treatment device;
   a venous line container which is arranged in the venous line following the blood treatment device;
   a sensor device for detecting an amount of treated blood being above a limit value in the venous line container;
   a sensor device for detecting an amount of untreated blood being below a limit value in the arterial line container;
   an arterial line closure device for closing the arterial line with simultaneous opening of the venous line in response to a first signal which is transmitted by the sensor device to the arterial line closure device;
   a venous line closure device for closing the venous line with simultaneous opening of the arterial line in response to a second signal which is transmitted by the sensor device to a venous line closure device; and
   at least one pump for conveying a phase volume $V_{Phase}$ with a pumping rate $Q_{BP}$, wherein
   if the actually conveyed phase volume $V_{act}$ deviates from a nominal phase volume $V_{nom}$, the control device regulates the pumping rate $Q_{Bp}$ of the at least one pump so that this deviation $\Delta V$, tends to be nil.

2. Apparatus according to claim 1 wherein the control device is designed as control circuit with which the automatic adjustment of the actual value $V_{act}$ a of the phase volume to its nominal value $V_{nom}$ and the associated change of the time period of a phase $t_{phase}$, can be performed in the venous phase as well as in the arterial phase.

3. Apparatus according to claim 1 wherein the controller of the control circuit is a P-controller, I-controller, D-controller, PI-controller, PD-controller, PID-controller, two-point controller, three-point controller, multi-point controller or fuzzy-controller.

4. Apparatus according to claim 1 wherein the nominal value $V_{nom}$, of the phase volume is at least 5 times larger than a dead volume $V_{dead}$, of the single-lumen-arrangement.

5. Apparatus according to claim 1 wherein the control device delays the regulation to the phase volume directly after detection of a deviation $\Delta V$ not equal to 0 of the actual value $V_{act}$, of the phase volume from its nominal value $V_{nom}$. by a predetermined dead time $T_{dead}$.

6. Apparatus according to claim 4 wherein the predetermined dead time $T_{dead}$ is between two phases, and 10 phases.

7. Apparatus according to claim 1 wherein the at least one pump is arranged between the arterial line container and the venous line container.

8. Apparatus according to claim 1 wherein the sensor devices pressure sensors.

9. Apparatus according to claim 1 wherein the over-pressure in the venous line container measured by the sensor device triggers a closing of the arterial line closure device and an opening of the venous line closure device and that wherein the under-pressure in the arterial line container measured by the sensor device triggers a closing of the venous line closure device and an opening of the arterial line closure device.

10. Apparatus according to claim 1 wherein for determination of the actual value $V_{act}$ of the phase volume, the pumping rate $Q_{BP}$. of the pump as well as the time period of a phase $t_{Phase}$ is used, wherein the time period of the phase $t_{Phase}$ is defined as a sum of the time period $t_{Ven-Phase}$, between the first signal and the second signal, which are transmitted by the control device to the arterial line closure device and the venous line closure device, and the time period $t_{Art-Phase}$ between the second signal and the first signal which are transmitted by the control device to the arterial line closure device and the venous line closure device.

* * * * *